United States Patent [19]

Ariyoshi et al.

[11] Patent Number: 5,650,544
[45] Date of Patent: Jul. 22, 1997

[54] PROCESS FOR PRODUCTION OF UNSATURATED ETHER AND CATALYST USED FOR PRODUCTION OF UNSATURATED ETHER

[75] Inventors: Kimio Ariyoshi, Suita; Yuuji Shimasaki, Otsu, both of Japan

[73] Assignee: Nippon Shokubai Co., Ltd., Osaka, Japan

[21] Appl. No.: 528,859

[22] Filed: Sep. 15, 1995

[30] Foreign Application Priority Data

Sep. 19, 1994 [JP] Japan .................. 6-222894

[51] Int. Cl.⁶ .................................................. C07C 41/28
[52] U.S. Cl. .................. 568/673; 568/616; 568/685; 568/698
[58] Field of Search ................... 568/616, 673, 568/685, 698

[56] References Cited

U.S. PATENT DOCUMENTS

| | | | |
|---|---|---|---|
| 3,480,605 | 11/1969 | Pittman et al. | 260/91.1 |
| 4,337,366 | 6/1982 | Fattore et al. | 568/698 |
| 5,100,852 | 3/1992 | Arntz et al. | |

FOREIGN PATENT DOCUMENTS

| | | |
|---|---|---|
| 0228898 | 7/1987 | European Pat. Off. . |
| 0227461 | 7/1987 | European Pat. Off. . |
| 62-87247 | 4/1987 | Japan . |
| 63-45651 | 9/1988 | Japan . |
| 495040 | 3/1992 | Japan . |
| 4198144 | 7/1992 | Japan . |
| 1735264 | 5/1992 | U.S.S.R. . |
| 0997958 | 7/1965 | United Kingdom . |

OTHER PUBLICATIONS

The Canadian Journal of Chem. Engineering, 1977, vol. 55, No. 3 pp. 341–346.

*Primary Examiner*—Gary Geist
*Assistant Examiner*—Sreeni Padmanabhan
*Attorney, Agent, or Firm*—Sherman and Shalloway

[57] ABSTRACT

The present invention provides a process for producing an unsaturated ether, which comprises subjecting a glycol ether to intramolecular dehydration in a gas phase in the presence of a catalyst to convert the glycol ether into an unsaturated ether directly in a one-step reaction. As the catalyst, an oxide containing, for example, silicon and an alkali metal is used. The process, which uses no auxiliary raw material, can produce an unsaturated ether (a vinyl ether and/or an allyl ether) simply and safely without generating any waste material derived from the auxiliary raw material.

10 Claims, No Drawings

PROCESS FOR PRODUCTION OF UNSATURATED ETHER AND CATALYST USED FOR PRODUCTION OF UNSATURATED ETHER

The present invention relates to a novel process for producing an unsaturated ether (a vinyl ether and/or an allyl ether) from a glycol ether, as well as to a catalyst used in said process. Hereinafter, the "unsaturated ether" mentioned in the present invention refers to a vinyl ether and/or an allyl ether unless otherwise specified.

Unsaturated ethers are useful as a raw material for polymers, organic synthetic substances, etc. Vinyl ethers, in particular, have wide applications and are useful as a raw material for synthetic resins, adhesives, etc., or as a raw material for organic synthetic substances such as glutaraldehyde and the like.

The present invention provides a process for producing an unsaturated ether, which comprises subjecting a glycol ether to intramolecular dehydration in a gas phase in the presence of a catalyst to convert the glycol ether into an unsaturated ether directly in a one-step reaction. The process, which uses no auxiliary raw material, can produce an unsaturated ether simply and safely without generating any waste material derived from the auxiliary raw material.

No technique has hitherto existed which can convert a glycol ether into an unsaturated ether in a gas phase with a catalyst, directly in a one-step reaction.

For production of a vinyl ether from a glycol ether (a raw material), indirect dehydration processes are known which comprise converting a glycol ether into an ester type intermediate and then decomposing the intermediate to obtain a vinyl ether. For example, in Can. J. Chem. Eng., 1977, Vol. 55, No. 3, pp. 341–346 is reported a process via an acetic acid ester intermediate. In the process, as shown in the following reaction scheme, a glycol ether and acetic anhydride are reacted in the presence of a zinc chloride catalyst to synthesize an ester, and the ester is subjected to pyrolysis in a gas phase to obtain a vinyl ether and acetic acid.

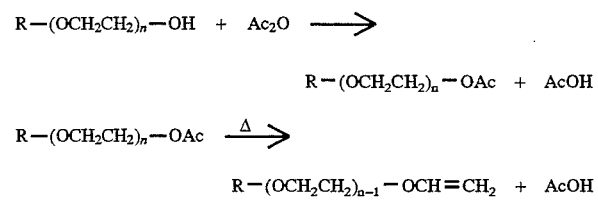

This process, however, is difficult to practise in industry because acetic anhydride is required in an amount equivalent to that of the raw material (glycol ether) and acetic acid is generated as a by-product in an amount equivalent to that of the product (vinyl ether).

Also in SU 1735264 A1 is disclosed an indirect dehydration process in a liquid phase, i.e. a reaction in an aqueous solution containing a glycol ether, KOH and KHSO$_4$ (the amounts of KOH and KHSO$_4$ are each at least one equivalent per equivalent of glycol ether). It is understood that the following reaction scheme takes place in the process, that is, a glycol ether is reacted with KHSO$_4$ to form its ester with sulfuric acid and the ester is decomposed into a vinyl ether and K$_2$SO$_4$ by the action of KOH.

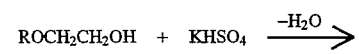

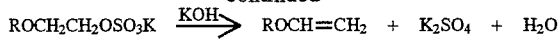

Thus, in the process, the auxiliary raw materials are required each in an amount at least equivalent to that of glycol ether; moreover, a large amount of a waste solution and a large amount of K$_2$SO$_4$ are generated. Therefore, the process is low in productivity and economy and is difficult to practise in industry.

Of unsaturated ethers, vinyl ethers are currently in industrial production by the following two processes.

One is a process of subjecting acetal to alcohol elimination, as shown in the following reaction formula.

This process includes a process using a Na-exchanged zeolite, disclosed in Japanese Patent Application Kokai (Laid-Open) No. 87247/1987 (=U.S. Pat. No. 5,100,852) and a process using a lithium phosphate, disclosed in Japanese Patent Publication No. 45651/1988. This process is advantageous in that neither auxiliary raw material nor solvent is required, but has various problems. That is, an alcohol of an amount equivalent to that of vinyl ether is generated as a by-product and the separation and recovery of the by-product requires much labor and a large expense; further, the raw material acetal is not easy to procure and is very expensive.

The other is a so-called Reppe process employing an addition reaction between acetylene and an alcohol, as shown in the following reaction formula.

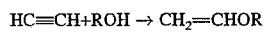

This process is conducted using an alkali catalyst in a liquid phase under pressure, but has a problem in that the reaction requires a complex control because acetylene may cause decomposition and explosion at high temperatures. Processes having slight improvements in solvent, catalyst and reaction pressure are disclosed in Japanese Patent Application Kokai (Laid-Open) Nos. 95040/1992 and 198144/1992. In these processes, however, a high-boiling solvent must be used and pressurization at 1.5–1.9 kg/cm$^2$ requires an expensive pressure reactor. Further, since the reaction is greatly influenced by the water content and raw material concentration in reaction system, complex operational controls such as (1) removal of the water accumulated in reaction system with feeding of raw material and (2) keeping raw material concentration at constant level are necessary in order to maintain a high reaction rate.

Meanwhile, as to the production of an allyl ether from a glycol ether, a process is known which comprises reacting allyl alcohol with an alkyl alcohol in the presence of an acid catalyst such as sulfuric acid, toluenesulfonic acid or the like to synthesize an allyl ether. The process, however, has a problem in that a dialkyl ether and diallyl ether are generated as by-products in large amounts, making low the selectivity of an intended allyl ether.

Also, a process is well known which comprises reacting a metal alcoholate (e.g. sodium methoxide or sodium ethoxide) with allyl chloride to selectively synthesize an allyl ether. The process, however, has a problem in that since an inorganic salt of an amount equivalent to that of produced allyl ether is generated as a by-product, the separation and disposal thereof requires much labor and a large expense.

As explained above, the conventional techniques for production of unsaturated ether are not satisfactory in industry. Hence, a process has been strongly desired which can produce an unsaturated ether from the raw material alone using neither solvent nor auxiliary raw material, directly in a one-step reaction.

The objects of the present invention are to provide a process for producing an unsaturated ether simply and safely, wherein a glycol ether of low cost and high availability can be converted into an unsaturated ether, directly in a one-step reaction, in the presence of a catalyst using neither raw material nor solvent; and a catalyst used in said process.

The present inventors made an extensive study on a process which alleviates the above-mentioned problems of conventional techniques and which can produce an unsaturated ether simply, safely and at a low cost. As a result, the present inventors found out that glycol ethers, when subjected to intramolecular dehydration in a gas phase in the presence of an oxide catalyst, are converted to respective unsaturated ethers and that an oxide containing at least one element selected from the group consisting of the elements of groups IVb, Vb, VIb, IIIa, IVa and Va of the periodic table exhibits an excellent catalytic activity in the above intramolecular dehydration.

According to the present invention, there is provided a process for producing an unsaturated ether, which comprises subjecting a glycol ether to intramolecular dehydration in a gas phase in the presence of a catalyst to convert the glycol ether into an unsaturated ether.

According to the present invention, there is also provided a catalyst used to produce an unsaturated ether by subjecting a glycol ether to intramolecular dehydration in a gas phase, which catalyst is an oxide containing at least one element selected from the group consisting of the elements of groups IVb, Vb, VIb, IIIa, IVa and Va of the periodic table.

The present invention is hereinafter described in detail.

In the process of the present invention, a reaction represented by the following reaction formula (6) and/or (7) is conducted in a gas phase.

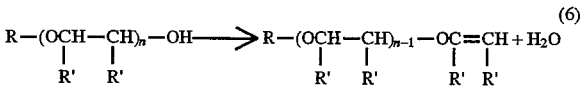

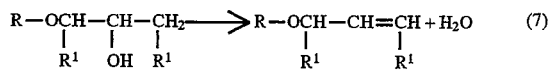

The reaction formula (6) represents a reaction for producing a vinyl ether, wherein the raw material glycol ether must be such as is represented by the following general formula (2):

(wherein R is a group selected from the group consisting of a hydrocarbon group having 1–7 carbon atoms and a perfluoroalkyl group having 1–8 carbon atoms; a plurality of R's are independently a group selected from the group consisting of a hydrogen atom, a methyl group and an ethyl group; and n 1 or 2) and such as can be fed into a catalyst layer as a vapor under the reaction conditions. Examples of the glycol ether are (a) 2-methoxyethanol, (b) 2-ethoxyethanol, (c) 2-isopropoxyethanol, (d) 2-butoxyethanol, (e) 2-isobutoxyethanol, (f) 2-hexyloxyethanol, (g) 2-benzyloxyethanol, (h) 2-methoxyethyloxyethanol, (i) 2-(1H,1H-perfluorobutyoxy) ethanol and (j) 2-(1H,1H,2H,2H-perflourooctyloxy)ethanol. The glycol ether is not restricted thereto. Incidentally, the glycol ethers (i) and (j) are represented by the following chemical formulas.

These glycol ethers, when subjected to intramolecular dehydration in a gas phase in the presence of the present catalyst, are converted into respective vinyl ethers represented by the following general formula (3):

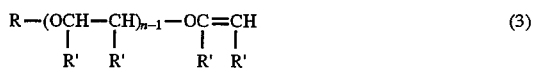

(wherein R, R' and n have the same definitions as given above), at a high yield and stably over a long period of time. Specifically explaining, the above glycol ethers (a) to (j) are converted into (a') methyl vinyl ether, (b') ethyl vinyl ether, (c') isopropyl vinyl ether, (d') butyl vinyl ether, (e') isobutyl vinyl ether, (f') hexyl vinyl ether, (g') benzyl vinyl ether, (h') methoxyethyl vinyl ether, (i') 1H,1H-perflourobutyl vinyl ether and (j') 1H,1H,2H,2H-perfluorooctylvinyl ether, respectively.

The reaction formula (7) represents a reaction for producing an allyl ether, wherein the raw material glycol ether must be such as is represented by the following general formula (4):

(wherein R is a hydrocarbon group having 1–7 carbon atoms, and two $R^1$s are independently a hydrogen atom or a methyl group) and such as can be fed into a catalyst layer as a vapor under the reaction conditions. Examples of the glycol ether are (k) 1-methoxy-2-propanol (l) 1-methoxy-2-butanol (m) 1-ethoxy-2-propanol and (n) 1-ethoxy-2-butanol. The glycol ether is not restricted thereto.

These glycol ethers, when subjected to intramolecular dehydration in a gas phase in the presence of the present catalyst, are converted into respective allyl ethers represented by the following general formula (5):

(wherein R and $R^1$ have the same definitions as given above), at a high yield and stably over a long period of time. Specifically explaining, the above glycol ethers (k) to (n) are converted into (k') 3-methoxy-1-propene, (l') 3-methoxy-1-butene, (m') 3-ethoxy-1-propene and (n') 3-ethoxy-1-butene, respectively.

The catalytic activity of the present catalyst is hardly deteriorated even when the catalyst is continuously used in a long-period reaction. Even if the catalyst is deteriorated owing to the coking, etc., the catalyst can recover its activity by burning the coke in the air.

Glycol ethers, when subjected to a high-temperature gas-phase reaction using a strongly acidic catalyst generally used in dehydration, tend to cause cleavage at the ether bond site and generate large amounts of by-products such as alcohol (derived from the alkoxyl moiety of glycol ether) and aldehyde or ketone (derived from the alkanol moiety), resulting in substantially no formation of an intended unsaturated ether. When the present catalyst is used, however, an intended unsaturated ether is formed. When there is used, as the catalyst, an oxide containing silicon and an alkali metal, in particular, the cleavage of ether bond is suppressed and the gas-phase intramolecular dehydration of glycol ether proceeds selectively, whereby an intended unsaturated ether is formed at a very high yield.

The catalyst used in the present process is an oxide containing at least one element selected from the group consisting of the elements of groups IVb, Vb, VIb, IIIa, IVa and Va of the periodic table. Preferable of these elements are B, Al, Si, P, Sb, Zr, Nb, W, etc. but are not restricted thereto.

The catalyst is preferably an oxide containing (1) at least one element selected from the group consisting of the elements of groups IVb, Vb, VIb, IIIa, IVa and Va of the periodic table and (2) an alkali metal.

The catalyst is more preferably an oxide containing (1) at least one element selected from the group consisting of the elements of groups IVb, Vb, VIb, IIIa, IVa and Va of the periodic table and (2) an alkali metal, wherein the atomic ratio of (2) to (1) is more than 0 (zero) but not more than 2, preferably more than 0 but not more than 1.

The catalyst is particularly preferably is an oxide containing silicon and an alkali metal, preferably represented by the following general formula (1)

$$M_aSi_bX_cO_d \quad (1)$$

wherein M is an alkali metal; Si is silicon; X is at least one element selected from the group consisting of Ti, Zr, V, Nb, Ta, Cr, Mo, W, B, Al, Ga, In, Tl, Ge, Sn, Pb, P and Sb; O is oxygen; a, b, c and d are each the number of atoms of the corresponding element with provisos that when a=1, b=1–500 and c=0–1 and that d is a number determined by the values of a, b and c and the condition in which the individual constituent elements are bonded to each other.

There is no particular restriction as to the method for preparation of the present catalyst, and any conventional method can be applied. Examples thereof are a method which comprises kneading the oxides or hydroxides of catalyst constituent elements with a molding aid such as water, alcohol or the like, followed by molding, drying and calcination; a method which comprises adding a base to an aqueous solution of salts (e.g. nitrates, carbonates, carboxylates and halides) of catalyst constituent elements to give rise to precipitation, collecting the resulting precipitate by filtration, and drying and calcinating the precipitate; and a method which comprises loading the above aqueous solution on a carrier (e.g. silica gel, alumina or silicon carbide) or mixing the aqueous solution with the carrier and then drying and calcinating the resulting material. In preparation of the present catalyst, the calcination temperature differs depending upon the kinds of the catalyst raw materials used, but is 300°–1,000° C., preferably 400°–800° C.

There is no particular restriction, either, as to the method for preparation of the particularly preferable catalyst of the present invention which is an oxide containing silicon and an alkali metal, and a method of ordinary use can be applied. The raw material for silicon can be silicon oxide, silicic acid, a silicic acid salt (e.g. an alkali metal silicate or an alkaline earth metal silicate), a silicon-containing molecular sieve (e.g. aluminosilicate or silicoaluminophosphate), an organic silicic acid ester, etc. The raw material for alkali metal can be an oxide, a hydroxide, a halide, a salt (e.g. a carbonate, a nitrate, a carboxylate, a phosphate or a sulfate), a metal itself, etc. The raw material for the third constituent element X added as necessary can be an oxide, a hydroxide, a halide, a salt (e.g. a carbonate, a nitrate, a carboxylate, a phosphate or a sulfate), a metal itself, etc.

Specific examples of the method for preparation of the particularly preferable catalyst of the present invention are described below.

(1) A method which comprises dissolving or suspending, in water, a raw material for alkali metal and a raw material for silicon, concentrating the aqueous solution or suspension with heating and stirring, followed by drying, molding and calcination, to obtain a catalyst.

(2) A method which comprises dissolving, in water, a raw material for alkali metal, dipping molded silicon oxide in the aqueous solution, followed by evaporation to dryness, drying and calcination, to obtain a catalyst.

(3) A method which comprises dissolving, in water, a raw material for alkali metal, mixing the aqueous solution with a silicic acid salt or a silicon-containing oxide, followed by drying, molding and calcination, to obtain a catalyst.

(4) A method which comprises doping a silicon-containing molecular sieve with an alkali metal by ion exchange, followed by drying, molding and calcination, to obtain a catalyst.

When the third constituent element X is allowed to be present in the catalyst, the element X may be present already in the raw material for alkali metal and/or in the raw material for silicon. Or, the raw material for the element X may be added independently in the course of the catalyst preparation.

Said catalyst may be supported on a known carrier such as alumina, silicon carbide or the like, or may be used in admixture with said carrier.

The temperature employed in calcination of catalyst differs depending upon the kinds of catalyst raw materials used, but can be in a wide range of 300°–1,000° C. and preferably in the range of 400°–800° C.

The process according to the present invention can be carried out in any reactor of fixed bed type or fluidized bed type. The reaction is conducted in such a pressure and temperature that the raw material, i.e. a glycol ether can maintain a gaseous state. The reaction pressure is generally normal pressure or reduced pressure. An applied pressure may be used. The reaction temperature differs depending upon the kinds of the raw materials and other conditions, but appropriately is 300°–600° C., preferably 350°–500° C. When the reaction temperature is lower than 300° C., the conversion of raw material glycol ether is significantly low; when the reaction temperature is higher than 600° C., the selectivity of intended unsaturated ether is significantly low. The raw material gas containing a glycol ether is diluted with a substance inert to the reaction, such as nitrogen, helium, argon, hydrocarbon or the like and/or the reaction system is made vacuum, whereby the raw material gas is fed into a catalyst layer with the partial pressure of glycol ether being controlled at 5–600 mmHg. The gas hourly space velocity (GHSV) of raw material glycol ether differs depending upon the kind of raw material and other conditions and is 1–1,000 h$^{-1}$, preferably 10–500 h$^{-1}$.

The present invention is hereinafter described specifically by way of Examples. However, the present invention is in no way restricted to the Examples.

Incidentally, the conversion, selectivity and per-pass yield used in the Examples have the following definitions.

Conversion (mole %)=100×[moles of consumed glycol ether]/[moles of fed glycol ether]

Selectivity (mole %)=100×[moles of produced unsaturated ether]/[moles of consumed glycol ether]

Per-pass yield (%)=100×[moles of produced unsaturated ether]/ [moles of fed glycol ether]

EXAMPLE 1

(Catalyst preparation)

30.0 g of silicon oxide was kneaded with 20 g of water. The mixture was dried in the air at 120° C. for 20 hours. The resulting solid was crushed into particles of 9–16 mesh and calcinated in the air at 500° C. for 2 hours to prepare a catalyst.

(Reaction)

10 ml of the catalyst was fed into a stainless steel-made reaction tube having an inside diameter of 10 mm. The reaction tube was immersed in a molten salt bath of 370° C. Into the reaction tube was fed a raw material gas consisting of 2-ethoxyethanol and nitrogen used as a diluent (the partial pressure of 2-ethoxyethanol in the raw material gas was 38 mmHg) at a space velocity (of 2-ethoxyethanol) of 75 h, to conduct a reaction at normal pressure. The reaction product after 1 hour from the start of raw material gas feeding was analyzed by gas chromatography. As a result, the conversion of 2-ethoxyethanol and the selectivity and per-pass yield of ethyl vinyl ether were 31.7 mole %, 4.2 mole % and 1.3 mole %, respectively.

EXAMPLE 2

(Catalyst preparation)

A catalyst was prepared in the same manner as in Example 1 except that silicon oxide was changed to 30 g of niobium pentoxide and the calcination temperature was changed to 700° C.

(Reaction)

A reaction was conducted with the catalyst in the same manner as in Example 1 except that the reaction temperature was changed to 400° C. After 1 hour from the start of raw material gas feeding, the conversion of 2-ethoxyethanol and the selectivity and per-pass yield of ethyl vinyl ether were 49.7 mole %, 12.3 mole % and 6.1 mole %, respectively.

EXAMPLE 3

(Catalyst preparation)

7.8 g of cesium nitrate and 4.2 g of diammonium phosphate were dissolved in 40 g of water. Thereto was added 26.6 g of niobium pentoxide. The mixture was concentrated to dryness with heating and mixing on a hot water bath. The resulting material was dried in the air at 120° C. for 20 hours, crushed to particles of 9–16 mesh, and calcinated in the air at 500° C. for 2 hours, to prepare a catalyst having a composition of $Cs_1P_{0.8}Nb_5$ in terms of atomic ratio when oxygen was excluded.

(Reaction)

A reaction was conducted with the catalyst in the same manner as in Example 1 except that the reaction temperature was changed to 420° C. After 1 hour from the start of raw material gas feeding, the conversion of 2-ethoxyethanol and the selectivity and per-pass yield of ethyl vinyl ether were 12.2 mole %, 46.3 mole % and 5.6 mole %, respectively.

EXAMPLE 4

(Catalyst preparation)

A catalyst having a composition of $Cs_1P_{0.8}Zr_5$ in terms of atomic ratio when oxygen was excluded, was prepared in the same manner as in Example 3 except that niobium pentoxide was changed to 24.7 g of zirconium oxide.

(Reaction)

A reaction was conducted with the catalyst in the same manner as in Example 1 except that the reaction temperature was changed to 450° C. After 1 hour from the start of raw material gas feeding, the conversion of 2-ethoxyethanol and the selectivity and per-pass yield of ethyl vinyl ether were 19.5 mole %, 65.1 mole % and 12.7 mole %, respectively.

EXAMPLE 5

(Catalyst preparation)

20 g of aluminum nitrate norahydrate and 6.2 g of orthophosphoric acid (content: 85% by weight) were dissolved in 100 g of water. Thereto was dropwise added 147 ml of a 28% by weight aqueous ammonia solution at room temperature in about 2 hours. The resulting precipitate was collected by filtration, washed thoroughly, and dried in the air at 120° C. for 20 hours. The resulting solid was crushed into particles of 9–16 mesh and calcinated in the air at 500° C. for 2 hours to prepare a catalyst having a composition of $Al_1P_1$ in terms of atomic ratio when oxygen was excluded.

(Reaction)

A reaction was conducted with the catalyst in the same manner as in Example 1 except that the reaction temperature was changed to 300° C. After 1 hour from the start of raw material gas feeding, the conversion of 2-ethoxyethanol and the selectivity and per-pass yield of ethyl vinyl ether were 95.8 mole %, 17.2 mole % and 16.5 mole %, respectively.

EXAMPLE 6

(Catalyst preparation)

1.95 g of cesium nitrate was dissolved in 10 g of water. The solution was kneaded with 23.2 g of tungsten oxide. The resulting material was dried in the air at 120° C. for 20 hours and then calcinated in the air at 500° C. for 2 hours to prepare a catalyst having a composition of $Cs_1W_{10}$ in terms of atomic ratio when oxygen was excluded.

(Reaction)

A reaction was conducted with the catalyst in the same manner as in Example 1 except that the reaction temperature was changed to 430° C. After 1 hour from the start of raw material gas feeding, the conversion of 2-ethoxyethanol and the selectivity and per-pass yield of ethyl vinyl ether were 12.9 mole %, 38.1 mole % and 4.9 mole %, respectively.

EXAMPLE 7

(Catalyst preparation)

A catalyst having a composition of $Cs_1Sb_{10}$ in terms of atomic ratio when oxygen was excluded, was prepared in the same manner as in Example 6 except that tungsten oxide was changed to 14.6 g of antimony trioxide.

(Reaction)

A reaction was conducted with the catalyst in the same manner as in Example 1 except that the reaction temperature was changed to 430° C. After 1 hour from the start of raw material gas feeding, the conversion of 2-ethoxyethanol and the selectivity and per-pass yield of ethyl vinyl ether were 37.2 mole %, 20.8 mole % and 7.7 mole %, respectively.

EXAMPLE 8

(Catalyst preparation)

A catalyst having a composition of $Cs_1Mo_{10}$ in terms of atomic ratio when oxygen was excluded, was prepared in the same manner as in Example 6 except that 3.9 g of cesium nitrate was dissolved in 20 g of water and then 28.8 g of molybdenum trioxide was added to the solution, followed by kneading.

(Reaction)

A reaction was conducted with the catalyst in the same manner as in Example 1 except that the reaction temperature was changed to 430° C. After 1 hour from the start of raw material gas feeding, the conversion of 2-ethoxyethanol and the selectivity and per-pass yield of ethyl vinyl ether were 44.3 mole %, 11.3 mole % and 5.0 mole %, respectively.

EXAMPLE 9

(Catalyst preparation)

A catalyst having a composition of $Cs_1Ti_{10}$ in terms of atomic ratio when oxygen was excluded, was prepared in the same manner as in Example 6 except that 3.9 g of nitrate was dissolved in 20 g of water and then 16.0 g of titanium dioxide was added to the solution, followed by kneading.

(Reaction)

A reaction was conducted with the catalyst in the same manner as in Example 1 except that the reaction temperature was changed to 430° C. After 1 hour from the start of raw material gas feeding, the conversion of 2-ethoxyethanol and the selectivity and per-pass yield of ethyl vinyl ether were 15.7 mole %, 15.3 mole % and 2.4 mole %, respectively.

EXAMPLE 10

(Catalyst preparation)

19.5 g of cesium nitrate and 4.9 g of boric acid were dissolved in 100 g of water. Thereto was added 30.0 g of silicon oxide. The mixture was concentrated to dryness with heating on a hot water bath. The resulting material was dried in the air at 120° C. for 20 hours, crushed into particles of 9–16 mesh and calcinated in the air at 500° C. for 2 hours, to prepare a catalyst having a composition of $Cs_1Si_5B_{0.8}$ in terms of atomic ratio when oxygen was excluded.

(Reaction)

A reaction was conducted with the catalyst in the same manner as in Example 1 except that the reaction temperature was changed to 410° C. After 1 hour from the start of raw material gas feeding, the conversion of 2-ethoxyethanol and the selectivity and per-pass yield of ethyl vinyl ether were 28.2 mole %, 71.4 mole % and 20.1 mole %, respectively.

EXAMPLE 11

3.45 g of lithium nitrate was dissolved in 50 g of water. Thereto was added 30 g of silicon oxide with heating and stirring. The mixture was concentrated with heating The concentrate was dried in the air at 120° C. for 20 hours. The resulting solid was crushed into particles of 9–16 mesh and calcinated in the air at 500° C. for 2 hours to prepare a catalyst having a composition of $Li_1Si_{10}$ in terms of atomic ratio when oxygen was excluded.

(Reaction)

10 ml of the catalyst was fed into a stainless steel-made reaction tube having an inside diameter of 10 mm. The reaction tube was immersed in a molten salt bath of 450° C. Into the reaction tube was fed a raw material gas consisting of 2-ethoxyethanol and nitrogen used as a diluent (the partial pressure of 2-ethoxyethanol in the raw material gas was 38 mmHg) at a space velocity (of 2-ethoxyethanol) of 75 h, to conduct a reaction at normal pressure. The reaction product after 1 hour from the start of raw material gas feeding was analyzed by gas chromatography. As a result, the conversion of 2-ethoxyethanol and the selectivity and per-pass yield of ethyl vinyl ether were 15.5 mole %, 22.8 mole % and 3.5 mole %, respectively.

EXAMPLES 12–15

(Catalyst preparation)

Catalysts having the compositions (each expressed in terms of atomic ratio when oxygen was excluded) shown in Table 1 were prepared in the same manner as in Example 11 except that 3.45 g of lithium nitrate used in Example 11 was changed to 4.25 g of sodium nitrate (Example 12), 5.06 g of potassium nitrate (Example 13), 7.38 g of rubidium nitrate (Example 14) and 9.75 g of cesium nitrate (Example 15).

(Reactions)

Reactions were conducted with these catalysts in the same manner as in Example 11 except that the reaction temperature was changed. After 1 hour from the start of raw material gas feeding, the conversions of 2-ethoxyethanol and the selectivities and per-pass yields of ethyl vinyl ether were as shown in Table 1.

TABLE 1

| Example No. | Catalyst | Reaction temp. (°C.) | Conversion (mole %) | Selectivity (mole %) | Per-pass yield (mole %) |
|---|---|---|---|---|---|
| 12 | $Na_1Si_{10}$ | 450 | 14.3 | 38.3 | 5.5 |
| 13 | $K_1Si_{10}$ | 450 | 70.5 | 79.6 | 56.1 |
| 14 | $Rb_1Si_{10}$ | 420 | 41.5 | 85.8 | 35.6 |
| 15 | $Cs_1Si_{10}$ | 420 | 72.5 | 84.4 | 61.2 |

EXAMPLE 16

(Catalyst preparation)

2.50 g of cesium hydroxide was dissolved in 40 g of water. In the solution was immersed 30 g of spherical silica gel (5–10 mesh) for 2 hours. The mixture was heated to dryness on a hot water bath. The resulting material was dried in the air at 120° C. for 20 hours and then calcinated in the air at 500° C. for 2 hours to prepare a catalyst having a composition of $Cs_1Si_{30}$ in terms of atomic ratio when oxygen was excluded.

(Reaction)

A reaction was conducted with the catalyst in the same manner as in Example 11 except that the reaction temperature was changed to 420° C. After 1 hour, 20 hours and 50 hours from the start of raw material gas feeding, the conversions of 2-ethoxyethanol and the selectivities and per-pass yields of ethyl vinyl ether were as shown in Table 2.

TABLE 2

| Time (hour) | Conversion (mole %) | Selectivity (mole %) | Per-pass yield (mole %) |
|---|---|---|---|
| 1 | 83.8 | 91.7 | 76.8 |
| 20 | 81.7 | 92.3 | 75.4 |
| 50 | 80.8 | 93.4 | 75.5 |

EXAMPLES 17–19

Reactions were conducted with the catalyst of Example 16 in the same manner as in Example 11 except that the reaction condition used in Example 11 was changed to those shown in Table 3. After 1 hour from the start of raw material gas feeding, the conversions of 2-ethoxyethanol and the selectivities and per-pass yields of ethyl vinyl ether were as shown in Table 3.

TABLE 3

| Ex. No. | Material partial pressure (mmHg) | Space velocity (hr$^{-1}$) | Reaction temp. (°C.) | Conversion (mole %) | Selectivity (mole %) | Per-pass yield (mole %) |
| --- | --- | --- | --- | --- | --- | --- |
| 17 | 76 | 150 | 450 | 82.0 | 89.7 | 73.6 |
| 18 | 38 | 25  | 410 | 84.7 | 92.5 | 78.3 |
| 19 | 38 | 150 | 430 | 80.8 | 91.9 | 74.3 |

EXAMPLE 20

(Catalyst preparation)

A catalyst having a composition of $K_1Si_{50}$ in terms of atomic ratio when oxygen was excluded, was prepared in the same manner as in Example 16 except that 2.50 g of cesium hydroxide was changed to 0.561 g of potassium hydroxide.

(Reaction)

A reaction was conducted with the catalyst in the same manner as in Example 11 except that the reaction temperature was changed to 420° C. After 1 hour from the start of raw material gas feeding, the conversion of 2-ethoxyethanol and the selectivity and per-pass yield of ethyl vinyl ether were 65.8 mole %, 82.1 mole % and 54.0 mole %, respectively.

EXAMPLE 21

(Catalyst preparation)

A catalyst having a composition of $Cs_1Si_{100}$ in terms of atomic ratio when oxygen was excluded, was prepared in the same manner as in Example 16 except that 2.50 g of cesium hydroxide was changed to 0.81 g of cesium carbonate.

(Reaction)

A reaction was conducted with the catalyst in the same manner as in Example 11 except that the reaction temperature was changed to 420° C. After 1 hour from the start of raw material gas feeding, the conversion of 2-ethoxyethanol and the selectivity and per-pass yield of ethyl vinyl ether were 80.3 mole %, 85.0 mole % and 68.3 mole %, respectively.

EXAMPLE 22

(Catalyst preparation)

A catalyst having a composition of $Cs_1Si_{200}$ in terms of atomic ratio when oxygen was excluded, was prepared in the same manner as in Example 16 except that 2.50 g of cesium hydroxide was changed to 0.41 g of cesium carbonate.

(Reaction)

A reaction was conducted with the catalyst in the same manner as in Example 11 except that the reaction temperature was changed to 430° C. After 1 hour from the start of raw material gas feeding, the conversion of 2-ethoxyethanol and the selectivity and per-pass yield of ethyl vinyl ether were 69.8 mole %, 84.2 mole % and 58.8 mole %, respectively.

EXAMPLE 23

(Catalyst preparation)

A catalyst having a composition of $Na_{0.5}K_{0.5}Si_{30}$ in terms of atomic ratio when oxygen was excluded, was prepared in the same manner as in Example 16 except that 2.50 g of cesium hydroxide was changed to 0.33 g of sodium hydroxide and 0.47 g of potassium hydroxide.

(Reaction)

A reaction was conducted with the catalyst in the same manner as in Example 11. After 1 hour from the start of raw material gas feeding, the conversion of 2-ethoxyethanol and the selectivity and per-pass yield of ethyl vinyl ether were 62.2 mole %, 77.7 mole % and 48.3 mole %, respectively.

EXAMPLE 24

(Catalyst preparation)

17.9 g of disodium hydrogenphosphate dodecahydrate was dissolved in 100 g of water. Thereto was added 30 g of silicon oxide. The mixture was concentrated to dryness with heating and stirring on a hot water bath. The resulting material was dried in the air at 120° C. for 20 hours, crushed into particles of 9–16 mesh, and calcinated in the air at 400° C. for 2 hours to prepare a catalyst having a composition of $Na_1Si_5P_{0.5}$ in terms of atomic ratio when oxygen was excluded.

(Reaction)

A reaction was conducted with the catalyst in the same manner as in Example 11 except that the reaction temperature was changed to 420° C. After 1 hour from the start of raw material gas feeding, the conversion of 2-ethoxyethanol and the selectivity and per-pass yield of ethyl vinyl ether were 23.8 mole %, 59.4 mole % and 14.1 mole %, respectively.

EXAMPLES 25–34

(Catalyst preparation)

9.75 g of cesium nitrate and 5.28 g of diammonium phosphate were dissolved in 100 g of water. Thereto was added 30 g of silicon oxide. The mixture was concentrated to dryness with heating and stirring on a hot water bath. The resulting material was dried in the air at 120° C. for 20 hours, crushed into particles of 9–16 mesh, and calcinated in the air at 500° C. for 2 hours to prepare a catalyst having a composition of $Cs_1Si_{10}P_{0.8}$ in terms of atomic ratio when oxygen was excluded.

(Reaction)

Reactions were conducted with the catalyst in the same manner as in Example 11 except that the raw material for reaction was 2-ethoxyethanol (Example 25), 2-methoxyethanol (Example 26), 2-butoxyethanol (Example 27), 2-n-hexyloxyethanol (Example 28), 2-isopropoxyethanol (Example 29), 2-isobutoxyethanol (Example 30), 2-benzyloxyethanol (Example 31), 2-methoxyethyloxyethanol (Example 32), 2-(1H,1H-perfluorobutyloxy)ethanol (Example 33) and 2-(1H,1H,2H,2H-perfluorooctyloxy)ethanol (Example 34). After 1 hour from the start of raw material gas feeding, the conversions of raw materials and the selectivities and per-pass yields of vinyl ethers were as shown in Table 4.

TABLE 4

| Ex. No. | Raw material glycol ether | Conversion (mole %) | Selectivity (mole %) | Per-pass yield (mole %) |
| --- | --- | --- | --- | --- |
| 25 | 2-Ethoxyethanol | 38.5 | 89.6 | 34.5 |
| 26 | 2-Methoxyethanol | 52.2 | 91.0 | 47.5 |
| 27 | 2-Butoxyethanol | 84.6 | 88.2 | 74.6 |
| 28 | 2-n-Hexyloxyethanol | 95.8 | 96.6 | 92.5 |
| 29 | 2-Isopropoxyethanol | 54.4 | 93.8 | 51.0 |
| 30 | 2-Isobutoxyethanol | 42.1 | 95.3 | 40.1 |
| 31 | 2-Benzyloxyethanol | 46.4 | 86.7 | 40.2 |

TABLE 4-continued

| Ex. No. | Raw material glycol ether | Conversion (mole %) | Selectivity (mole %) | Per-pass yield (mole %) |
|---|---|---|---|---|
| 32 | 2-Methoxyethyloxy-ethanol | 44.2 | 92.7 | 41.0 |
| 33 | 2-(1H,1H-Perfluoro-butyloxy)ethanol | 53.2 | 92.4 | 49.2 |
| 34 | 2-(1H,1H,2H,2H-Per-fluorooctyloxy)-ethanol | 64.4 | 93.7 | 60.3 |

EXAMPLES 35–38 (Production of allyl ethers)

Reactions were conducted with the same catalyst and reaction conditions as in Example 25 except that the raw material for reaction, used in Example 25 was changed to 1-methoxy-2-propanol (Example 35), 1-ethoxy-2-propanol (Example 36), 1-methoxy-2-butanol (Example 37) and 1-ethoxy-2-butanol (Example 38). In each Example, two kinds of unsaturated ethers, i.e. a vinyl ether and an allyl ether were formed. After 1 hour from the start of raw material gas feeding, the conversions of raw materials and the selectivities and per-pass yields of unsaturated ethers formed were as shown in Table 5.

TABLE 5

| Ex. No. | Raw material glycol ether | Conversion (mole %) | Unsaturated ether formed | Selectivity (mole %) | Per-pass yield (mole %) |
|---|---|---|---|---|---|
| 35 | 1-Methoxy-2-propanol | 46.8 | 3-Methoxy-2-propene | 22.0 | 10.3 |
|  |  |  | 3-Methoxy-1-propene | 64.0 | 30.0 |
| 36 | 1-Ethoxy-2-propanol | 50.0 | 3-Ethoxy-2-propene | 23.2 | 11.6 |
|  |  |  | 3-Ethoxy-1-propene | 66.0 | 33.0 |
| 37 | 1-Methoxy-2-butanol | 43.9 | 3-Methoxy-2-butene | 21.8 | 9.6 |
|  |  |  | 3-Methoxy-1-butene | 63.1 | 27.7 |
| 38 | 1-Ethoxy-2-butanol | 48.2 | 3-Ethoxy-2-butene | 24.4 | 11.8 |
|  |  |  | 3-Ethoxy-1-butene | 65.1 | 31.4 |

EXAMPLE 39

(Catalyst preparation)

Using 3.25 g of cesium nitrate, 0.44 g of diammonium phosphate and 30 g of silicon oxide, there was prepared, in the same manner as in Example 16, a catalyst having a composition of $Cs_1Si_{30}P_{0.2}$ in terms of atomic ratio when oxygen was excluded.

(Reaction)

A reaction was conducted with the catalyst in the same manner as in Example 11 except that the reaction temperature was changed to 430° C. After 1 hour from the start of raw material gas feeding, the conversion of 2-ethoxyethanol and the selectivity and per-pass yield of ethyl vinyl ether were 70.4 mole %, 88.3 mole % and 62.2 mole %, respectively.

EXAMPLE 40

(Reaction)

A reaction was conducted in the same manner as in Example 39 except that 2-ethoxyethanol was changed to 2-methoxyethanol After 1 hour from the start of raw material gas feeding, the conversion of 2-methoxyethanol and the selectivity and per-pass yield of methyl vinyl ether were 72.7 mole %, 92.1 mole % and 67.0 mole %, respectively.

EXAMPLE 41

(Catalyst preparation)

9.75 g of cesium nitrate and 2.67 g of zirconyl nitrate dihydrate were dissolved in 100 g of water. Thereto was added 30 g of silicon oxide. The mixture was concentrated to dryness with heating and stirring on a hot water bath. The resulting material was dried in the air at 120° C. for 20 hours, crushed into particles of 9–16 mesh, and calcinated in the air at 500° C. for 2 hours to prepare a catalyst having a composition of $Cs_1Si_{10}Zr_{0.2}$ in terms of atomic ratio when oxygen was excluded.

(Reaction)

A reaction was conducted with the catalyst in the same manner as in Example 11. After 1 hour from the start of raw material gas feeding, the conversion of 2-ethoxyethanol and the selectivity and per-pass yield of ethyl vinyl ether were 57.3 mole %, 86.4 mole % and 49.5 mole %, respectively.

EXAMPLE 42

(Catalyst preparation)

5.06 g of potassium nitrate and 4.05 g of niobium pentachloride were dissolved in 100 g of water. Thereto was added 30 g of silicon oxide. The mixture was concentrated to dryness with heating and stirring on a hot water bath. The resulting material was dried in the air at 120° C. for 20 hours, crushed into particles of 9–16 mesh, and calcinated in the air at 500° C. for 2 hours to prepare a catalyst having a composition of $K_1Si_{10}Nb_{0.3}$ in terms of atomic ratio when oxygen was excluded.

(Reaction)

A reaction was conducted with the catalyst in the same manner as in Example 11. After 1 hour from the start of raw material gas feeding, the conversion of 2-ethoxyethanol and the selectivity and per-pass yield of ethyl vinyl ether were 62.3 mole %, 83.1 mole % and 51.8 mole %, respectively.

EXAMPLE 43

(Catalyst preparation)

4.64 g of an aqueous ammonium metatungstate solution (containing tungsten in an amount of 50% by weight in terms of tungsten trioxide) and 7.5 g of cesium hydroxide were mixed with 100 g of water. Thereto was added 30 g of silicon oxide. The mixture was concentrated to dryness with heating and stirring on a hot water bath. The resulting material was dried in the air at 120° C. for 20 hours, crushed into particles of 9–16 mesh, and calcinated in the air at 500° C. for 2 hours to prepare a catalyst having a composition of $Cs_1Si_{10}W_{0.2}$ in terms of atomic ratio when oxygen was excluded.

(Reaction)

A reaction was conducted with the catalyst in the same manner as in Example 11. After 1 hour from the start of raw material gas feeding, the conversion of 2-ethoxyethanol and the selectivity and per-pass yield of ethyl vinyl ether were 62.1 mole %, 87.3 mole % and 54.2 mole %, respectively.

EXAMPLE 44

(Catalyst preparation)

9.75 g of cesium nitrate was dissolved in 100 g of water. Thereto were added 1.53 g of aluminum phosphate and 30 g of silicon oxide. The mixture was concentrated to dryness with heating and stirring on a hot water bath. The resulting material was dried in the air at 120° C. for 20 hours, crushed into particles of 9–16 mesh, and calcinated in the air at 500° C. for 2 hours to prepare a catalyst having a composition of $Cs_1Si_{10}Al_{0.25}P_{0.25}$ in terms of atomic ratio when oxygen was excluded.

(Reaction)

A reaction was conducted with the catalyst in the same manner as in Example 11. After 1 hour from the start of raw material gas feeding, the conversion of 2-ethoxyethanol and the selectivity and per-pass yield of ethyl vinyl ether were 65.8 mole %, 85.1 mole % and 56.0 mole %, respectively.

EXAMPLE 45

(Catalyst preparation)

4.87 g of cesium nitrate and 0.33 g of diammonium phosphate were dissolved in 40 g of water. Therein was immersed 30 g of a spherical silica gel (5–10 mesh) for 2 hours. The resulting material was heated to dryness on a hot water bath, followed by drying in the air at 120° C. for 20 hours and subsequent calcination in the air at 700° C. for 2 hours, to prepare a catalyst having a composition of $Cs_1Si_{20}P_{0.1}$ in terms of atomic ratio when oxygen was excluded.

(Reaction)

A reaction was conducted with the catalyst in the same manner as in Example 11 except that the reaction temperature was changed to 430° C. After 1 hour from the start of raw material gas feeding, the conversion of 2-ethoxyethanol and the selectivity and per-pass yield of ethyl vinyl ether were 78.7 mole %, 94.1 mole % and 74.1 mole %, respectively.

EXAMPLE 46

10 ml of the catalyst of Example 16 was filled into a stainless steel-made reaction tube. The reaction tube was immersed in a molten salt bath of 420° C. The inside of the reaction tube was made vacuum by the use of a vacuum pump, and 2-ethoxyethanol was fed into the reaction tube under the conditions of reaction tube outlet pressure =50 mmHg and 2-ethoxyethanol space velocity =100 hr$^{-1}$. A reaction was conducted for 100 hours continuously. Then, the feeding of raw material was stopped; nitrogen was introduced to release the pressure; air was passed through the reaction tube for 24 hours to burn and remove the carbonaceous substance deposited on the catalyst, whereby the catalyst was regenerated. Thereafter, a reaction was conducted for 100 hours continuously under the same conditions as mentioned above. After 1 hour, 20 hours and 100 hours from the start of raw material feeding and after 1 hour, 20 hours and 100 hours from the catalyst regeneration, the conversions of 2-ethoxyethanol and the selectivities and per-pass yields of ethyl vinyl ether were as shown in Table 6.

TABLE 6

| Time (hour) | Conversion (mole %) | Selectivity (mole %) | Per-pass yield (mole %) |
| --- | --- | --- | --- |
| 1 | 86.2 | 92.1 | 79.4 |
| 20 | 81.2 | 93.8 | 76.2 |
| 100 | 80.1 | 94.6 | 75.8 |

TABLE 6-continued

| Time (hour) | Conversion (mole %) | Selectivity (mole %) | Per-pass yield (mole %) |
| --- | --- | --- | --- |
| After regeneration | | | |
| 1 | 86.9 | 92.6 | 80.5 |
| 20 | 82.1 | 94.5 | 77.6 |
| 100 | 80.7 | 95.1 | 76.7 |

As illustrated with the above Examples, the catalyst of the present invention enables continuous and one-step production of an unsaturated ether (a vinyl ether and/or an allyl ether) from a glycol ether using no auxiliary raw material. Therefore, the present process for production of an unsaturated ether is simple because no auxiliary raw material is used, and is safe because no waste substance derived from said auxiliary raw material is generated.

What is claimed is:

1. A process for producing vinyl or allyl ether, which comprises subjecting a 1,2-glycol monoether to intramolecular dehydration in a gas phase in the presence of an oxide containing at least one element selected from the group consisting of the elements of groups IVb, Vb, VIb, IIIa, IVa and Va of the periodic table, as a catalyst therefor.

2. A process according to claim 1, wherein the catalyst is an oxide containing an alkali metal.

3. A process according to any of claim 1 or 2, wherein the catalyst is an oxide containing silicon and an alkali metal.

4. A process according to any of claim 3, wherein the catalyst is an oxide represented by the following general formula (1)

$$M_aSi_bX_cO_d \qquad (1)$$

wherein M is an alkali metal; Si is silicon; X is at least one element selected from the group consisting of Ti, Zr, V, Nb, Ta, Cr, Mo, W, B, Al, Ga, In, Tl, Ge, Sn, Pb, P and Sb; O is oxygen; a, b, c and d are each the number of atoms of the corresponding element with provisos that when a=1, b=1–500 and c=0–1 and that d is a number determined by the values of a, b and c and the condition in which the individual constituent elements are bonded to each other.

5. A process according to claim 1 or 2, wherein the 1,2-glycol monoether is represented by the following general formula (2):

$$R-(OCH-CH)_n-OH \qquad (2)$$
$$\quad\; | \quad\;\; | $$
$$\quad R' \quad R'$$

(wherein R is a group selected from the group consisting of a hydrocarbon a group having 1–7 carbon atoms and a perfluoroalkyl group having 1–8 carbon atoms; a plurality of R's are independently a group selected from the group consisting of a hydrogen atom, a methyl group and an ethyl group; and n is 1 or 2), and the vinyl ether is represented by the following general formula (3):

$$R-(OCH-CH)_{n-1}-OC=CH \qquad (3)$$
$$\quad\; | \quad\;\; | \quad\;\;\; | \quad\; |$$
$$\quad R' \quad R' \quad R' \quad R'$$

(wherein R, R' and n have the same definitions as given above.).

6. A process according to claim 1 or 3, wherein the 1,2-glycol monoether is represented by the following general formula (4):

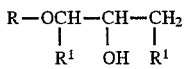  (4)

(wherein R is a hydrocarbon group having 1–7 carbon atoms, and two R¹s are independently a hydrogen atom or a methyl group), and the allyl ether is represented by the following general formula (5):

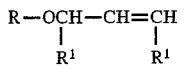  (5)

(wherein R and R¹ have the same definitions as given above).

7. A process according to claim 3, wherein the 1,2-glycol monoether is represented by the following general formula (2):

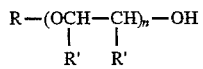  (2)

(wherein R is a group selected from the group consisting of a hydrocarbon group having 1–7 carbon atoms and a perfluoroalkyl group having 1–8 carbon atoms; a plurality of R's are independently a group selected from the group consisting of a hydrogen atom, a methyl group and an ethyl group; and n is 1 or 2), and the vinyl ether is represented by the following general formula (3):

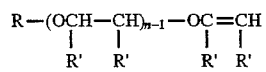  (3)

(wherein R, R' and n have the same definitions as given above).

8. A process according to claim 3, wherein the 1,2-glycol monoether is represented by the following general formula (4):

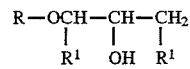  (4)

(wherein R is a hydrocarbon group having 1–7 carbon atoms, and two R¹s are independently a hydrogen atom or a methyl group), and the allyl ether is represented by the following general formula (5):

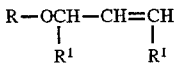  (5)

(wherein R and R¹ have the same definitions as given above).

9. A process according to claim 4 wherein the 1,2-glycol monoether is represented by the following general formula (2):

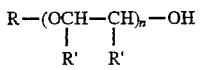  (2)

(wherein R is a group selected from the group consisting of a hydrocarbon group having 1–7 carbon atoms and a perfluoralkyl group having 1–8 carbon atoms; a plurality of R's are independently a group selected from the group consisting of a hydrogen atom, a methyl group and an ethyl group; and n is 1 or 2), and the vinyl ether is represented by the following general formula (3):

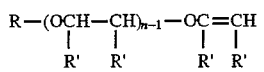  (3)

(wherein R, R' and n have the same definitions as given above).

10. A process according to claim 4, wherein the 1,2-glycol monoether is represented by the following general formula (4):

R—OCH—CH—CH₂ (4)
  |    |    |
  R¹   OH   R¹

(wherein R is a hydrocarbon group having 1–7 carbon atoms, and two R¹s are independently a hydrogen atom or a methyl group), and the allyl ether is represented by the following general formula (5):

R—OCH—CH=CH (5)
  |        |
  R¹       R¹

(wherein R and R¹ have the same definitions as given above).

* * * * *